United States Patent [19]

Sheinaus et al.

[11] Patent Number: 4,505,862

[45] Date of Patent: Mar. 19, 1985

[54] DIPHENYDRAMINE DIHYDROGENCITRATE

[75] Inventors: Harold Sheinaus, Watchung; Arnold D. Marcus, Livingston, both of N.J.

[73] Assignee: Bristol-Myers Company, New York, N.Y.

[21] Appl. No.: 417,820

[22] Filed: Sep. 13, 1982

Related U.S. Application Data

[62] Division of Ser. No. 254,036, Apr. 14, 1981, Pat. No. 4,401,665.

[51] Int. Cl.³ ............................................. C07C 97/10
[52] U.S. Cl. ............................... 260/501.18; 568/583; 568/585; 562/584
[58] Field of Search ...................... 260/501.17, 501.18; 568/583, 585; 562/584

[56] References Cited

U.S. PATENT DOCUMENTS

| | | |
|---|---|---|
| 2,238,149 | 4/1941 | Aeckerle ............................ 562/584 |
| 2,370,552 | 2/1945 | Lincoln et al. ...................... 568/583 |
| 2,427,887 | 9/1947 | Wallace . |
| 2,481,406 | 9/1949 | Ferguson . |
| 2,801,951 | 8/1957 | Cooper . |
| 3,024,165 | 3/1962 | Murphy . |
| 3,058,987 | 10/1962 | Albrecht et al. ............... 260/501.17 |
| 3,068,147 | 12/1962 | Emele . |
| 3,080,287 | 3/1963 | Lewenstein . |
| 3,161,567 | 12/1964 | Collins et al. . |
| 3,282,778 | 11/1966 | Lobel . |
| 3,336,193 | 8/1967 | Valery . |
| 3,567,819 | 3/1971 | Idson et al. . |
| 3,703,519 | 11/1972 | Henderson . |
| 4,025,624 | 5/1977 | Alphin et al. . |
| 4,044,125 | 8/1977 | Walkling . |
| 4,049,803 | 9/1977 | Cotty et al. ........................ 424/233 |
| 4,083,950 | 4/1978 | Duvall et al. . |

OTHER PUBLICATIONS

OTC Sedative Panel Report, vol. 37, A-1 to A-3, Dec. 8, 1975, FDC Reports, "The Pink Sheet".
OTC Sedative Panel Report, vol. 36, p. 16, Nov. 11, 1974, FDC Reports, "The Pink Sheet".

*Primary Examiner*—Alton D. Rollins
*Assistant Examiner*—Raymond Covington
*Attorney, Agent, or Firm*—Gabriel P. Katona

[57] ABSTRACT

An analgesic and sleep-aid composition containing an analgesic (e.g. aspirin, APAP or combinations thereof) and diphenhydramine dihydrogencitrate. Discloses several dosage forms including a two layer tablet in which aspirin is contained in one layer and APAP contained in the other layer; the preferred form being such that the diphenhydramine dihydrogencitrate is contained in the APAP layer.

1 Claim, No Drawings

DIPHENYDRAMINE DIHYDROGENCITRATE

This is a division of application Ser. No. 254,036, filed Apr. 14, 1981, now U.S. Pat. No. 4,401,665.

This invention relates to an analgesic and sleep aid composition containing an analgesic (e.g. aspirin, acetaminophen (APAP) or combinations thereof) and diphenhydramine dihydrogencitrate. It also concerns diphenhydramine dihydrogencitrate as a novel compound which may be expressed by the formula:

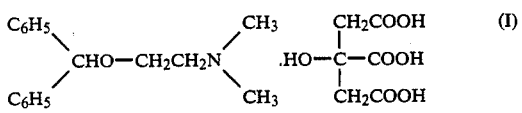

It is known in the prior art to formulate so-called "nighttime analgesics" consisting of an aspirin layer and an APAP layer; the latter also containing methapyrilene fumarate. A tablet of this character is described in the "Physicians Desk Reference" 28th Edition, 1974, page 640, column 3 (published by Medical Economics Company, a Litton Division, Oradell, New Jersey). In these tablets, the methapyrilene fumarate is believed to function as a sleep-aid; whereas, the aspirin and APAP are thought to play their usual roles.

These tablets have proven to be effective in the past for their intended purposes. Recently, however, some negative opinion has developed with respect to the safety of methapyrilene fumarate. This led to a search for a drug which might replace it in these tablets.

In the course of this search, Applicants attempted to formulate tablets of the above described type which made use of a widely employed antihistamine i.e. diphenhydramine hydrochloride. This is the hydrochloride salt of 2-diphenylmethoxy-N,N-dimethylethylamine and has the structure:

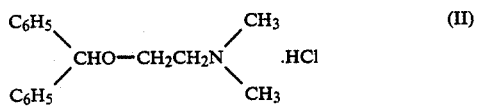

It was found, however, that when this was used to prepare the aforesaid tablets, the resulting products did not have acceptable chemical and physical stability or tabletting characteristics. Thus, for example, at room temperature and at elevated temperatures and at high humidity conditions, unacceptable discoloration and mottling of the APAP layer occurred. Similarly, at high temperature storage (125° F.), severe darkening also took place in the aspirin layer. In addition, other tabletting problems were encountered when the diphenhydramine hydrochloride was employed. Lubrication and compression problems were run into during the tabletting process and the tablets were unduly soft.

Efforts were also made to use other diphenhydramine salts in formulating the aforesaid tablets. Particularly, the salicylate and fumarate salt were employed. However, it was found that with these salts also, the resulting tablets were unsatisfactory resulting in soft, mottled and generally physically and chemically unstable tablets.

It has now been discovered, unexpectedly, that when the dihydrogencitrate salt of diphenhydramine is employed in preparing the above described tablets containing aspirin, APAP or combinations thereof, the stability of the resulting tablets was very significantly increased. This also has application to other dosage forms as, for example, when these materials are dispensed in the form of powders or granules contained in a capsule, packet, etc.

It is accordingly an object of the present invention to provide a relatively stable analgesic sleep-aid composition containing aspirin, APAP or combinations thereof and diphenhydramine dihydrogencitrate and a process for preparing the same.

It is also an object of the present invention to provide the novel diphenhydramine dihydrogencitrate salt.

Other and more detailed objects of the present invention will be apparent from the following description and claims.

As indicated above, the composition of the present invention will contain an analgesic component which may comprise aspirin, APAP or a combination of the two. The quantity of the analgesic component that will be contained within a dosage unit (e.g. tablet, capsule, etc.) will be enough so that the required dosage of analgesic can be delivered by the administration of a reasonable number of dosage units. Generally, the quantity of analgesic in a dosage unit in accordance with the present invention may vary from about 80 milligrams to about 1000 milligrams. This may be all aspirin, all APAP or some proportion of each.

When the aspirin and APAP are present in the composition, the weight ratio of aspirin to APAP can vary over a range (e.g. from about 0.2 to about 5). However, they will usually be used in about equal proportions by weight.

In the preferred aspects of the present invention, the quantity of analgesic which will be contained in the present composition will fall in the range of from about 450 mg. to about 600 mg. of analgesic. It is also preferred that both aspirin and APAP be contained in the composition and that they be used in about roughly equal proportions by weight i.e. the ratio of aspirin to APAP is in the range of from about 0.90 to 1.10.

The diphenhydramine dihydrogencitrate may be contained in the compositions of this invention in varying proportions depending on the quantity and nature of the other ingredients in the composition. Generally, however, it will be present in these compositions at a level of from about 17 mg. to 77 mg. (and preferably at a level of about 38.5 mg. per unit dose).

In a preferred aspect of the present invention, the product is prepared as a two layer tablet which comprises an aspirin layer and an APAP layer. In this instance too, the total analgesic contained in the tablet will generally be in the range of from about 80 mg. to about 1000 mg. with the preferred range being from about 450 mg. to 600 mg. Here also weight ratio of aspirin to APAP can vary over a wide range (e.g. from about 0.2 to about 5) with the preferred ratio being in the range of from about 0.90 to about 1.10.

In the two layered tablet, the diphenhydramine dihydrogencitrate may be distributed in the aspirin layer, or the APAP layer, or may be distributed in various proportions in both layers. Here again, the diphenhydramine dihydrogencitrate may be present in the two layered tablet at a level of from about 19 mg. to about 77 mg. with the preferred quantity being about 38.5 mg. In a preferred aspect of the invention, essentially all of diphenhydramine dihydrogencitrate is contained in the APAP layer.

It is useful also to express the relative quantities of the active ingredients contained in the two layered tablets with respect to the total weight of the tablet. Thus, the aspirin may constitute between about 15% to about 90% by weight based on the total weight of the tablet, with the preferred percentage being about 40% by weight. Similarly, the APAP may be present in the two layered tablet at a level of from about 15% to about 90% by weight based on the total weight of the tablet. Here too, the preferred level is about 40% by weight based on the total weight of the tablet.

The diphenhydramine dihydrogencitrate will usually constitute between about 3% to about 12% by weight based on the total weight of the two layered tablet. In this case, the preferred level of the diphenhydramine dihydrogencitrate will be about 6% on the same weight basis.

In the preferred procedure for preparing the aspirin layer in the two-layered tablet, aspirin is compacted with starch, such that the aspirin represents from 85% to 90% of the mixture, and the compact is reduced to granules of an appropriate size range for compression into tablets. A wetting agent such as sodium lauryl sulfate may be added, if desired, to further facilitate disintegration.

Usually, the starch will be present in the aspirin layer at a level of from 18 mg. to 150 mg. (preferably 25 mg.) and will constitute from about 10% to about 15% by weight of the aspirin layer (preferably 10%).

The APAP layer of the two layered tablet may also contain a disintegrating agent. Several disintegrating agents are known in the prior art which would be suitable for this purpose. Corn starch has proven to be very acceptable. The quantity of disintegrating agent that may be incorporated in the APAP layer may also vary somewhat. For the most part, however, this will be present in the range of from about 12 mg. to about 50 mg. per tablet and constitute from about 2% to about 8% by weight based on the total weight of the tablet.

In preparing the APAP layer, it is convenient to prepare a granulation of the active ingredients before compressing the ingredients to form the APAP layer. For this purpose, as in the preparation of the aspirin layer, it is useful to employ a granulating agent. Many granulating agents known to those skilled in this art can serve this purpose. However, pregelatinized starch is the preferred granulating agent which usually will be present in an amount in the range of from 5 mg. to 60 mg. per APAP layer and comprise about 1.5% to about 9% by weight of the finished APAP layer. Preferably, the level of pregelatinized starch will be about 15 mg. per APAP layer constituting about 4.5% by weight based on the weight of the APAP layer.

The APAP layer may be prepared in a variety of fashions. In one procedure, the diphenhydramine dihydrogencitrate is blended with a small quantity of a disintegrating agent (e.g. starch) which is then reduced to an appropriate particle size. This is then mixed with the APAP and pregelatinized starch and the mixture is granulated with water (or water solution containing the coloring agents). After drying and screening the granulation, the balance of disintegrating agent (e.g. starch) and the lubricating agent (e.g. hydrogenated castor oil powder) may be blended into the granulation and the mixture compressed to form the APAP layer.

Alternatively, a direct compression APAP product may be utilized. In this instance, the APAP has been preprocessed by the manufacturer to contain various ingredients such as starch, carboxymethyl starch, cellulose or other organic or inorganic materials to impart direct compression properties to it.

In addition, the tablets of the present invention may include the usual tablet additives e.g. lubricating agents, food grade coloring agents, etc. As an illustration of a lubricating agent that may be used herein, mention may be made of hydrogenated castor oil powder. This may be used at a level of from about 0.3% to about 1.3% by weight based on the total weight of the tablet.

The two layered tablet is prepared by filling the die cavity at the first filling station of a two layer tablet press with the appropriate amount of aspirin granulation, adding an appropriate amount of the APAP-diphenhydramine dihydrogencitrate granulation at the second filling station, and compressing the whole into a two layered tablet. Tamping lightly after first layer fill may be included.

In using the compositions of the present invention, one or more of the unit dosage forms described above would be taken by a subject who may be experiencing pain and difficulty in falling asleep. The number of unit dosage forms that will be taken will depend on the particular quantities of active ingredients contained in the dosage form and the dose of active ingredient that is recommended as being safe and effective. In the typical case, where the level of analgesic in a unit dosage form is about 500 mg. which consists of about equal parts by weight of aspirin and acetaminophen and the level of diphenhydramine dihydrogencitrate present is about 38.5 mg., two unit dosage forms (e.g. tablets) will be taken to obtain the desired effect.

The following Examples are given to further illustrate the present invention. It is to be understood, however, that the invention is not limited thereto.

EXAMPLE 1

Preparation of Diphenhydramine Dihydrogencitrate 1. 3 gm. diphenhydramine HCl dissolved in 20 ml. water.
2. Add 10N NaOH to pH 12, extract with 2×25 ml. ether.
3. Add and mix 2 gm. citric acid in 200 ml. ether to the ether extract of step 2; crystallize overnight in refrigerator.
4. Filter, wash with ether and air dry (M.P. 146.5°–148° C.).
5. Recrystallize from boiling anhydrous ethanol; filter, wash with anhydrous ethanol, and air dry (M.P. 147.5°–148.5° C.).

EXAMPLE 2

Preparation of Two-Layered Tablet CK 1566-50

| Ingredients | mg/tablet | % w/w |
|---|---|---|
| LAYER I | | |
| 1. Aspirin-Starch Gran. Blue | 277.778 | 45.5237 |
| LAYER II | | |
| 2. Acetaminophen, spec. powd. | 250.000 | 40.9713 |
| 3. Diphenhydramine dihydrogencitrate | 38.335 | 6.2825 |
| 4. Starch, corn | 15.000 | 2.4583 |
| 5. Starch, pregelatinized | 15.000 | 2.4583 |
| 6. Color, FD & C Blue #1 | 0.065 | 0.0107 |
| 7. Color, D & C Yellow #10 | 0.005 | 0.0008 |
| 8. Starch, corn | 10.000 | 1.6389 |
| 9. Castor oil, hydrog., | 4.000 | 0.6555 |

| Ingredients | mg/tablet | % w/w |
|---|---|---|
| powd. | | |
| 10. Water, deionized q.s. | | |
| | 332.405 | |
| | | 100.0000 |
| | 610.183 | |

LAYER I

A. Blend 9 parts aspirin with 1 part starch, previously colored blue with FD&C Blue #1.
B. Compact the mixture in a Chilsonator or other suitable compacting equipment.
C. Pass the compact through a size reduction apparatus (such as a Fitzmill or a Tornado mill) using a screen of proper mesh to give an appropriate size range of granules suitable for tabletting.

LAYER II

A. Preblend 3 and 4, pass through 30 mesh screen to reduce agglomerates.
B. Mix preblend A with 2 and 5, and granulate with a solution of 6 and 7 in cool water (approx. 500 ml/10,000 tablets).
C. Pass wet granulation through Tornado, 5/16" screen.
D. Dry in Fluid Bed Dryer using cool (R.T.) air to approx. 1% moisture (Ohaus).
E. Pass dry granulation through Oscillator, 0.078" opening screen.
F. Blend in 8 and 9, and this mixture is ready for compression as second layer.

The aspirin granulation prepared as described in Layer I above is fed into a die cavity at a first filling station. This material may be tamped down lightly and the die cavity containing this granulation is passed on to a second filling station where the appropriate amount of APAP granulation prepared as described above under Layer II is fed into the die. The die cavity containing the aspirin layer and APAP layer is then passed to a compression station where the two layers are compressed together with a tablet punch to form a two layered tablet.

To compare the relative merits of two layered tablets containing diphenhydramine dihydrogencitrate and diphenhydramine hydrochloride respectively, two compositions were prepared according to the procedure of Example 2 above. In the one case, the tablets had the composition shown in Example 2 containing the diphenhydramine dihydrogencitrate and this was identified by the code CK 1566-50. In the second case, the composition was the same as that shown in Example 2 excepting that an equimolar amount of diphenhydramine hydrochloride (25 mg.) replaced the diphenhydramine dihydrogencitrate and 25 mg. microcrystalline cellulose replaced the 15 mg. starch as item 4. This product was coded CK 1566-52.

Each of these products was evaluated as to problems in tabletting, hardness, disintegration rate, and appearance after aging under various conditions. The results of these tests are summarized in Table I below:

TABLE I

| | | CK 1566-50 (dihydrogencitrate) | CK 1566-52 (hydrochloride) |
|---|---|---|---|
| Tabletting | | No granulation or compression problems | Lubrication and compression problems; soft; weight variation |
| Hardness (Heberlein) | Initial | 10-11 SCU | 12-14 SCU |
| | 10 mo. @ R.T. | 11 SCU | 24-27 SCU |
| | 4 wk. @ 104° F. | 10-17 SCU at all conditions | 15-28 SCU at all conditions |
| | 4 wk. @ H/H | | |
| | 4 wk. @ 125° F. | | |
| Disintergration | Initial | <½ minute | 2¼ minutes |
| USP Basket, | 10 mo. @ R.T. | ½ minute | 11-11½ minutes |
| Water, 37° C. | 4 wk. @ 104° F. | ½ minute at all conditions | 5 minutes at all conditions |
| | 4 wk. @ H/H | | |
| | 4 wk. @ 125° F. | | |
| Appearance | 10 mo. @ R.T. | APAP layer - slight darkening and mottling at all conditions | APAP layer - unacceptable discoloration at all conditions |
| | 4 wk. @ 104° F. | | |
| | 4 wk. @ H/H | ASA layer - OK at all conditions | ASA layer - slight darkening at R.T., 104°F., and H/H Severe darkening at 125° F. |
| | 4 wk. @ 125° F. | | |

EXAMPLE 3

Formula #1164

Using the procedure given in Example 2, a two layered tablet was prepared having the following composition:

| Ingredients | mg/tablet | % w/w |
|---|---|---|
| LAYER I | | |
| 1. Aspirin-Starch Gran. Blue | 270.000 | 44.4517 |
| LAYER II | | |
| 2. Acetaminophen, spec. powd. | 243.000 | 40.0065 |
| 3. Diphenhydramine dihydrogencitrate | 38.335 | 6.3113 |
| 4. Starch, corn | 15.000 | 2.4695 |
| 5. Starch, pregelatinized | 15.000 | 2.4695 |
| 6. Color, FD & C Blue #1 | 0.060 | 0.0100 |
| 7. Color, FD & C Yellow #5 | 0.006 | 0.0010 |
| 8. Starch, corn | 20.000 | 3.2927 |
| 9. Castor oil, hydrog., powd. | 6.000 | 0.9878 |
| 10. Water, deionized q.s. | | |
| | 337.401 | |
| | | 1000.0000 |
| | 607.401 | |

EXAMPLE 4

Formula #1701

Using the procedure given in Example 2, a two layered tablet is prepared having the following composition:

| Ingredients | mg/tablet | % w/w |
|---|---|---|
| LAYER I | | |
| 1. Aspirin-Starch Gran. Blue | 277.778 | 44.7134 |
| LAYER II | | |
| 2. Acetaminophen, spec. powd. | 250.000 | 40.2420 |
| 3. Diphenhydramine dihydrogencitrate | 38.335 | 6.1707 |
| 4. Starch, pregelatinized | 15.000 | 2.4145 |
| 5. Povidone K-29-32 | 3.000 | 0.4829 |
| 6. Color, FDC Blue #1 | 0.120 | 0.0193 |
| 7. Color, FDC Yellow #10 | 0.008 | 0.0013 |
| 8. Cellulose, microcrystalline | 35.000 | 5.6339 |
| 9. Stearic acid, powd. | 2.000 | 0.3220 |
| | 343.463 | |
| | | 100.000 |
| | 621.241 | |

EXAMPLE 5

Using the procedure given in Example 2, the following two layered tablet is prepared:

| Ingredients | mg/tablet | % w/w |
|---|---|---|
| LAYER I | | |
| 1. Aspirin-Starch Gran. Blue | 277.778 | 44.7149 |
| LAYER II | | |
| 2. Acetaminophen, Direct Compression, 90% | 277.778 | 44.7149 |
| 3. Starch, corn | 25.000 | 4.0243 |
| 4. Diphenhydramine dihydrogencitrate | 38.335 | 6.1709 |
| 5. Color, FDC Blue #1 | 0.300 | 0.0483 |
| 6. Color, FDC Yellow #10 | 0.030 | 0.0048 |
| 7. Stearic acid, powd. | 2.000 | 0.3219 |
| | 343.443 | |
| | 621.221 | 100.0000 |

EXAMPLE 6

CK 1566-49

The following is an example of a one layer tablet containing only APAP as the analgesic:

| Ingredients | mg/tablet | % w/w |
|---|---|---|
| 1. Acetaminophen, spec. powd. | 500.000 | 79.8607 |
| 2. Diphenhydramine dihydrogencitrate | 38.335 | 6.1229 |
| 3. Microcrystalline cellulose | 50.000 | 7.9861 |
| 4. Starch, corn | 20.000 | 3.1944 |
| 5. Starch, pregelatinized | 10.000 | 1.5972 |
| 6. Povidone K-29-32 | 5.000 | 0.7986 |
| 7. Color, FDC Blue #1 | 0.051 | 0.0082 |
| 8. Color, FDC Yellow #10 | 0.004 | 0.0006 |
| 9. Methylparaben | 0.500 | 0.0799 |
| 10. Propylparaben | 0.200 | 0.0319 |
| 11. Stearic acid, powd. | 2.000 | 0.3195 |
| | 626.090 | 100.0000 |

EXAMPLE 7

The following is an example of a single layer tablet containing only aspirin as the analgesic:

| Ingredients | mg/tablet | % w/w |
|---|---|---|
| 1. Aspirin - 10% starch granulation | 555.555 | 93.231 |
| 2. Diphenhydramine dihydrogencitrate | 38.335 | 6.433 |
| 3. Stearic acid | 2.000 | 0.336 |
| | 595.890 | 100.000 |

Blend well and compress.

EXAMPLE 8

The following is an example of a single layer tablet containing APAP as the analgesic:

| Ingredients | mg/tablet | % w/w |
|---|---|---|
| 1. Acetaminophen, direct compression, 95% | 526.316 | 82.670 |
| 2. Diphenhydramine dihydrogencitrate | 38.335 | 6.021 |
| 3. Cellulose, microcrystalline | 50.000 | 7.854 |
| 4. Starch, corn | 20.000 | 3.141 |
| 5. Stearic acid | 2.000 | 0.314 |
| | 636.651 | 100.000 |

Blend well and compress.

EXAMPLE 9

The following is an example of a single layer tablet in which the analgesic is a mixture of aspirin and APAP:

| Ingredients | mg/tablet | % w/w |
|---|---|---|
| 1. Aspirin, 10% starch granulation | 277.778 | 46.198 |
| 2. Acetaminophen, direct compression, 95% | 263.158 | 43.767 |
| 3. Diphenhydramine dihydrogencitrate | 38.335 | 6.376 |
| 4. Starch, corn | 20.000 | 3.326 |
| 5. Stearic acid | 2.000 | 0.333 |
| | 601.271 | 100.000 |

Blend well and compress.

To compare the chemical stability of aspirin/APAP compositions containing diphenhydramine dihydrogencitrate with aspirin/APAP compositions containing diphenhydramine hydrochloride, the following formulas were prepared:

TABLE II

| | Formula # | |
|---|---|---|
| Active Agent | CK 1566-52 | CK 1566-50 |
| Aspirin | 250 mg | 250 mg |
| Acetaminophen | 250 mg | 250 mg |
| Diphenhydramine hydrochloride | 25 mg | — |
| Diphenhydramine dihydrogencitrate | — | 38.335 mg* |

*38.335 mg of diphenhydramine dihydrogencitrate is the molar equivalent of 25 mg of diphenhydramine hydrochloride The important measure of chemical stability in any product in which aspirin is combined with an amine salt is the rate of production of free salicylic acid produced by the degradation of aspirin. The higher the level of free salicylic acid, the more aspirin has degraded.

Formulas CK 1566-50 and CK 1566-52 were stored at various temperatures for various periods of time. At specified time intervals, samples of each formula were analyzed for free salicylic acid (FSA). The greater the amount of free salicylic acid found, the less stable the product. The results of this study are summarized in Table III below:

TABLE III

| Product # | Condition of Storage | Time | mg FSA |
|---|---|---|---|
| CK 1566-50 | 60° C./60% RH | 90 hrs. | 2.27 |
| CK 1566-52 | " | " | 4.85 |
| CK 1566-50 | 40° C./80% RH | 1 month | 0.38 |
| CK 1566-52 | " | " | 1.45 |
| CK 1566-50 | 50° C. | 1 month | 0.66 |
| CK 1566-52 | " | " | 3.0–4.6 |
| CK 1566-50 | R.T. | 11 months | 0.33 |
| CK 1566-52 | " | " | 0.95 |

Additionally, tablet CK 1566-50 containing diphenhydramine dihydrogencitrate exhibited a more rapid dissolution rate than tablet CK 1566-52 containing diphenhydramine hydrochloride, as may be seen from the following Table (2 tablets, 250 ml. water at 37° C., 50 RPM stirrer):

TABLE IV

Dissolution Rates of Diphenhydramine Salts from Tablets

| | Minutes | | |
|---|---|---|---|
| | T25 | T50 | T75 |
| CK 1566-50 (dihydrogencitrate) | 4.1 | 5.7 | 8.3 |
| CK 1566-52 (hydrochloride) | 10.4 | 13.1 | 18.1 |

Although the invention has been described with reference to specific forms thereof, it will be understood that many changes and modifications may be made without departing from the spirit of this invention.

What is claimed is:

1. Diphenhydramine dihydrogencitrate.

* * * * *